(12) United States Patent
Hannula et al.

(10) Patent No.: US 7,979,102 B2
(45) Date of Patent: Jul. 12, 2011

(54) HAT-BASED OXIMETER SENSOR

(75) Inventors: Don Hannula, San Luis Obispo, CA (US); Paul Mannheimer, Danville, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 1510 days.

(21) Appl. No.: 11/358,868

(22) Filed: Feb. 21, 2006

(65) Prior Publication Data

US 2006/0195028 A1 Aug. 31, 2006

Related U.S. Application Data

(62) Division of application No. 10/606,668, filed on Jun. 25, 2003, now Pat. No. 7,047,056.

(51) Int. Cl.
*A61B 5/1455* (2006.01)
(52) U.S. Cl. ........................ 600/340; 600/344
(58) Field of Classification Search .......... 600/310, 600/322, 323, 340, 344
See application file for complete search history.

(56) References Cited

U.S. PATENT DOCUMENTS

| | | | |
|---|---|---|---|
| 1,304,215 A * | 5/1919 | Snyder | 2/181 |
| 1,899,020 A * | 2/1933 | Drueding | 2/181 |
| 4,025,733 A | 5/1977 | Klar et al. | |
| 4,047,400 A | 9/1977 | Thorneburg | |
| 4,321,930 A * | 3/1982 | Jobsis et al. | 600/344 |
| 4,462,116 A | 7/1984 | Sanzone et al. | |
| 4,499,741 A | 2/1985 | Harris | |
| 4,510,938 A | 4/1985 | Jobsis et al. | |
| 4,570,638 A | 2/1986 | Stoddart et al. | |
| 4,675,919 A | 6/1987 | Heine et al. | |
| 4,739,757 A | 4/1988 | Edwards | |
| 4,775,116 A | 10/1988 | Klein | |
| 4,784,162 A | 11/1988 | Ricks et al. | |
| 4,802,485 A | 2/1989 | Bowers et al. | |
| 4,825,872 A | 5/1989 | Tan et al. | |
| 4,825,879 A | 5/1989 | Tan et al. | |
| 4,833,734 A | 5/1989 | Der Estephanian | |
| 4,838,279 A | 6/1989 | Fore | |
| 4,856,116 A | 8/1989 | Sullivan | |
| 4,890,619 A | 1/1990 | Hatschek | |
| 4,910,804 A | 3/1990 | Lidgren | |
| 4,918,758 A | 4/1990 | Rendina | |

(Continued)

FOREIGN PATENT DOCUMENTS

CN 1306260 8/2001

(Continued)

OTHER PUBLICATIONS

U.S. Appl. No. 10/677,742, filed Oct. 1, 2003, Hannula.

(Continued)

*Primary Examiner* — Eric F Winakur
(74) *Attorney, Agent, or Firm* — Fletcher Yoder

(57) ABSTRACT

A method for use and an improved oximeter sensor substrate that is conforming to the shape of the patient's forehead. In one embodiment, the present invention is an oximeter sensor, having a substrate with a shape similar to a shape of at least a portion of a patient's forehead and including a section adapted to substantially fit over a portion of a forehead of a patient; an emitter disposed on the substrate at a position located on the section; and a detector disposed on the substrate at a distance from the emitter. In one embodiment, the substrate includes a hat that holds the emitter and the detector in a spaced-part manner against the patient's forehead.

20 Claims, 3 Drawing Sheets

U.S. PATENT DOCUMENTS

| | | | |
|---|---|---|---|
| 4,930,888 A | 6/1990 | Feisleben et al. | |
| 4,942,877 A | 7/1990 | Sakai et al. | |
| 4,972,331 A | 11/1990 | Chance | |
| 4,977,011 A | 12/1990 | Smith | |
| 4,991,234 A | 2/1991 | Greenberg | |
| 4,996,975 A | 3/1991 | Nakamura | |
| 5,005,374 A | 4/1991 | Spitler | |
| 5,054,488 A | 10/1991 | Muz | |
| 5,080,096 A | 1/1992 | Hooper et al. | |
| 5,080,098 A | 1/1992 | Willett et al. | |
| H1039 H | 4/1992 | Tripp, Jr. et al. | |
| 5,111,817 A | 5/1992 | Clark et al. | |
| 5,119,815 A | 6/1992 | Chance | |
| 5,122,974 A | 6/1992 | Chance | |
| 5,125,403 A | 6/1992 | Culp | |
| 5,167,230 A | 12/1992 | Chance | |
| 5,188,108 A | 2/1993 | Secker | |
| 5,191,891 A | 3/1993 | Righter | |
| 5,209,230 A | 5/1993 | Swedlow et al. | |
| 5,214,409 A | 5/1993 | Beigel | |
| 5,217,012 A | 6/1993 | Young et al. | |
| 5,217,013 A | 6/1993 | Lewis et al. | |
| 5,241,300 A | 8/1993 | Buschmann | |
| 5,246,003 A | 9/1993 | DeLonzor | |
| 5,253,645 A | 10/1993 | Friedman et al. | |
| 5,267,563 A * | 12/1993 | Swedlow et al. | 600/323 |
| 5,267,567 A | 12/1993 | Aung et al. | |
| 5,295,490 A | 3/1994 | Dodakian | |
| 5,313,940 A | 5/1994 | Fuse et al. | |
| 5,337,744 A | 8/1994 | Branigan | |
| 5,348,008 A | 9/1994 | Bornn et al. | |
| 5,353,798 A | 10/1994 | Sieben | |
| 5,354,979 A | 10/1994 | Adelson et al. | |
| 5,357,953 A | 10/1994 | Merrick et al. | |
| 5,368,025 A | 11/1994 | Young et al. | |
| 5,368,562 A | 11/1994 | Blomquist et al. | |
| 5,369,808 A * | 12/1994 | Brewer et al. | 2/175.3 |
| 5,383,874 A | 1/1995 | Jackson et al. | |
| 5,392,777 A | 2/1995 | Swedlow et al. | |
| 5,398,689 A | 3/1995 | Connor et al. | |
| 5,400,267 A | 3/1995 | Denen et al. | |
| 5,405,269 A | 4/1995 | Stupecky | |
| 5,405,614 A | 4/1995 | D'Angelo et al. | |
| 5,413,099 A | 5/1995 | Schmidt et al. | |
| 5,413,101 A | 5/1995 | Sugiura | |
| 5,413,102 A | 5/1995 | Schmidt et al. | |
| 5,415,166 A | 5/1995 | Imran | |
| 5,425,360 A | 6/1995 | Nelson | |
| 5,431,170 A | 7/1995 | Mathews | |
| 5,437,275 A | 8/1995 | Amundsen et al. | |
| 5,437,634 A | 8/1995 | Amano | |
| 5,444,254 A | 8/1995 | Thomson | |
| 5,451,763 A | 9/1995 | Pickett et al. | |
| 5,452,717 A | 9/1995 | Branigan et al. | |
| 5,465,714 A * | 11/1995 | Scheuing | 600/323 |
| 5,469,845 A | 11/1995 | DeLonzor et al. | |
| 5,482,034 A * | 1/1996 | Lewis et al. | 600/323 |
| 5,490,523 A | 2/1996 | Isaacson et al. | |
| 5,507,752 A | 4/1996 | Elliott | |
| 5,528,519 A | 6/1996 | Onkura et al. | |
| 5,546,955 A | 8/1996 | Wilk | |
| 5,551,423 A | 9/1996 | Sugiura | |
| 5,562,718 A | 10/1996 | Palermo | |
| 5,564,108 A | 10/1996 | Hunsaker et al. | |
| 5,564,417 A | 10/1996 | Chance | |
| 5,584,296 A | 12/1996 | Cui et al. | |
| 5,592,408 A | 1/1997 | Keskin et al. | |
| 5,596,987 A | 1/1997 | Chance | |
| 5,617,865 A | 4/1997 | Palczewska et al. | |
| 5,617,866 A | 4/1997 | Marian, Jr. | |
| 5,627,323 A | 5/1997 | Stern | |
| 5,634,466 A | 6/1997 | Gruner | |
| 5,638,593 A | 6/1997 | Gerhardt et al. | |
| 5,638,818 A | 6/1997 | Diab et al. | |
| 5,640,953 A | 6/1997 | Bishop et al. | |
| 5,645,440 A | 7/1997 | Tobler et al. | |
| 5,645,586 A | 7/1997 | Meltzer | |
| 5,646,416 A | 7/1997 | Vande Velde | |
| 5,671,750 A | 9/1997 | Shinoda | |
| 5,673,708 A | 10/1997 | Athanasiou et al. | |
| 5,678,544 A | 10/1997 | DeLonzor et al. | |
| 5,681,285 A | 10/1997 | Ford et al. | |
| 5,683,434 A | 11/1997 | Archer | |
| 5,697,363 A | 12/1997 | Hart | |
| 5,697,367 A | 12/1997 | Lewis et al. | |
| 5,701,894 A | 12/1997 | Cherry et al. | |
| 5,706,820 A | 1/1998 | Hossack et al. | |
| 5,732,475 A | 3/1998 | Sacks et al. | |
| 5,738,612 A | 4/1998 | Tsuda | |
| 5,743,856 A | 4/1998 | Oka et al. | |
| 5,743,857 A | 4/1998 | Shinoda et al. | |
| 5,752,913 A | 5/1998 | Oka | |
| 5,752,920 A | 5/1998 | Ogura et al. | |
| 5,758,644 A | 6/1998 | Diab et al. | |
| 5,772,601 A | 6/1998 | Oka et al. | |
| 5,776,058 A | 7/1998 | Levinson et al. | |
| 5,776,071 A | 7/1998 | Inuka et al. | |
| 5,779,631 A | 7/1998 | Chance | |
| 5,779,639 A | 7/1998 | Yeung | |
| 5,782,757 A | 7/1998 | Diab et al. | |
| 5,786,592 A | 7/1998 | Hök | |
| 5,791,347 A | 8/1998 | Flaherty et al. | |
| 5,791,348 A | 8/1998 | Aung et al. | |
| 5,792,052 A | 8/1998 | Isaacson | |
| 5,792,058 A | 8/1998 | Lee et al. | |
| 5,797,841 A | 8/1998 | Delonzer et al. | |
| 5,810,724 A | 9/1998 | Gronvall | |
| 5,813,980 A | 9/1998 | Levinson et al. | |
| 5,817,008 A | 10/1998 | Rafert et al. | |
| 5,823,012 A | 10/1998 | Hacskaylo | |
| 5,823,952 A | 10/1998 | Levinson et al. | |
| 5,826,277 A | 10/1998 | McConville | |
| 5,830,136 A | 11/1998 | Delonzer et al. | |
| 5,830,137 A | 11/1998 | Scharf | |
| 5,830,148 A | 11/1998 | Inukai et al. | |
| 5,830,149 A | 11/1998 | Oka et al. | |
| 5,833,602 A | 11/1998 | Osemwota | |
| 5,836,887 A | 11/1998 | Oka et al. | |
| 5,839,439 A | 11/1998 | Nierlich et al. | |
| RE36,000 E | 12/1998 | Swedlow et al. | |
| 5,842,981 A | 12/1998 | Larsen et al. | |
| 5,842,982 A | 12/1998 | Mannheimer | |
| 5,851,179 A | 12/1998 | Ritson et al. | |
| 5,857,974 A | 1/1999 | Eberie et al. | |
| 5,860,932 A | 1/1999 | Goto et al. | |
| 5,860,957 A | 1/1999 | Jacobsen et al. | |
| 5,868,133 A | 2/1999 | DeVries et al. | |
| 5,870,626 A | 2/1999 | Lebeau | |
| 5,872,713 A | 2/1999 | Douglas et al. | |
| 5,873,821 A | 2/1999 | Chance et al. | |
| 5,879,294 A | 3/1999 | Anderson et al. | |
| 5,891,021 A | 4/1999 | Dillon et al. | |
| 5,891,026 A | 4/1999 | Wang et al. | |
| 5,895,359 A | 4/1999 | Peel, II | |
| 5,902,235 A | 5/1999 | Lewis et al. | |
| 5,906,581 A | 5/1999 | Tsuda | |
| 5,913,819 A | 6/1999 | Taylor et al. | |
| 5,916,154 A | 6/1999 | Hobbs et al. | |
| 5,919,133 A | 7/1999 | Taylor et al. | |
| 5,931,789 A | 8/1999 | Alfano et al. | |
| 5,931,790 A | 8/1999 | Peel, II | |
| 5,931,791 A | 8/1999 | Saltzstein et al. | |
| 5,934,925 A | 8/1999 | Tobler et al. | |
| 5,936,539 A | 8/1999 | Fuchs | |
| 5,947,905 A | 9/1999 | Hadjicostis et al. | |
| 5,954,053 A | 9/1999 | Chance et al. | |
| 5,957,850 A | 9/1999 | Marian, Jr. | |
| 5,964,701 A | 10/1999 | Asada et al. | |
| 5,980,464 A | 11/1999 | Tsuda | |
| 5,983,129 A | 11/1999 | Cowan et al. | |
| 5,987,343 A | 11/1999 | Kinast | |
| 5,987,351 A | 11/1999 | Chance | |
| 5,991,648 A | 11/1999 | Levin | |
| 5,995,077 A | 11/1999 | Wilcox et al. | |
| 5,995,855 A | 11/1999 | Kiani et al. | |
| 5,995,856 A | 11/1999 | Mannheimer et al. | |
| 5,995,857 A | 11/1999 | Toomim et al. | |

| | | | | | | |
|---|---|---|---|---|---|---|
| 6,007,492 | A | 12/1999 | Goto et al. | 6,417,774 B1 | 7/2002 | Hibbs et al. |
| 6,011,986 | A | 1/2000 | Diab et al. | 6,423,010 B1 | 7/2002 | Friedman et al. |
| 6,022,320 | A | 2/2000 | Ogura et al. | 6,430,423 B2 | 8/2002 | DeLonzer et al. |
| 6,027,453 | A | 2/2000 | Miwa et al. | 6,432,050 B1 | 8/2002 | Porat et al. |
| 6,030,351 | A | 2/2000 | Schmidt et al. | 6,450,168 B1 | 9/2002 | Nguyen |
| 6,031,603 | A | 2/2000 | Fine et al. | 6,450,957 B1 | 9/2002 | Yoshimi et al. |
| 6,036,651 | A | 3/2000 | Inukai et al. | 6,450,981 B1 | 9/2002 | Shabty et al. |
| 6,041,247 | A | 3/2000 | Weckstrom et al. | 6,454,708 B1 | 9/2002 | Ferguson et al. |
| 6,047,201 | A | 4/2000 | Jackson, III | 6,456,862 B2 | 9/2002 | Benni |
| 6,047,203 | A | 4/2000 | Sackner et al. | 6,461,305 B1 | 10/2002 | Schnall |
| 6,049,958 | A | 4/2000 | Eberle et al. | 6,463,310 B1 | 10/2002 | Swedlow et al. |
| 6,050,951 | A | 4/2000 | Friedman et al. | 6,466,809 B1 | 10/2002 | Riley |
| 6,052,619 | A | 4/2000 | John | 6,468,241 B1 | 10/2002 | Gelfand et al. |
| 6,073,038 | A | 6/2000 | Wang et al. | 6,470,199 B1 | 10/2002 | Kopotic et al. |
| 6,084,380 | A | 7/2000 | Burton | 6,470,279 B1 | 10/2002 | Samsoondar |
| 6,085,752 | A | 7/2000 | Kehr et al. | 6,480,762 B1 | 11/2002 | Uchikubo et al. |
| 6,088,607 | A | 7/2000 | Diab et al. | 6,491,638 B2 | 12/2002 | Oka |
| 6,106,780 | A | 8/2000 | Douglas et al. | 6,491,639 B1 | 12/2002 | Turcott |
| 6,112,107 | A | 8/2000 | Hannula | 6,503,087 B1 | 1/2003 | Eggert et al. |
| 6,115,621 | A | 9/2000 | Chin | 6,503,204 B1 | 1/2003 | Sumanaweera et al. |
| 6,118,382 | A | 9/2000 | Hibbs et al. | 6,505,061 B2 | 1/2003 | Larson |
| 6,134,459 | A | 10/2000 | Roberts et al. | 6,511,478 B1 | 1/2003 | Burnside et al. |
| 6,144,868 | A | 11/2000 | Parker | 6,516,289 B2 | 2/2003 | David |
| 6,149,481 | A | 11/2000 | Wang et al. | 6,519,487 B1 | 2/2003 | Parker |
| 6,152,754 | A | 11/2000 | Gerhardt et al. | 6,524,257 B2 | 2/2003 | Ogura |
| 6,154,667 | A | 11/2000 | Miura et al. | 6,525,386 B1 | 2/2003 | Mills et al. |
| 6,162,188 | A | 12/2000 | Barnea | 6,526,309 B1 | 2/2003 | Chance |
| 6,165,173 | A | 12/2000 | Kamdar et al. | 6,526,970 B2 | 3/2003 | DeVries et al. |
| 6,171,258 | B1 | 1/2001 | Karakasoglu et al. | 6,527,725 B1 | 3/2003 | Inukai et al. |
| 6,173,196 | B1 | 1/2001 | Delonzer et al. | 6,527,726 B2 | 3/2003 | Goto et al. |
| 6,179,786 | B1 | 1/2001 | Young | 6,535,765 B1 | 3/2003 | Amely-Velez et al. |
| 6,181,959 | B1 | 1/2001 | Schollermann et al. | 6,537,220 B1 | 3/2003 | Friemel et al. |
| 6,184,521 | B1 | 2/2001 | Coffin, IV et al. | 6,541,756 B2 | 4/2003 | Schulz et al. |
| 6,186,953 | B1 | 2/2001 | Narimatsu | 6,542,081 B2 | 4/2003 | Torch |
| 6,186,954 | B1 | 2/2001 | Narimatsu | 6,547,743 B2 | 4/2003 | Brydon |
| 6,190,325 | B1 | 2/2001 | Narimatsu | 6,551,252 B2 | 4/2003 | Sackner et al. |
| 6,196,974 | B1 | 3/2001 | Miwa | 6,553,242 B1 | 4/2003 | Sarussi |
| 6,198,952 | B1 | 3/2001 | Miesel | 6,575,902 B1 | 6/2003 | Burton |
| 6,199,550 | B1 | 3/2001 | Wiesmann et al. | 6,577,884 B1 | 6/2003 | Boas |
| 6,209,144 | B1 | 4/2001 | Carter | 6,580,086 B1 | 6/2003 | Schulz et al. |
| 6,216,021 | B1 | 4/2001 | Franceschini et al. | 6,582,371 B2 | 6/2003 | Miller |
| 6,223,063 | B1 | 4/2001 | Chaiken et al. | 6,582,374 B2 | 6/2003 | Yokozeki |
| 6,241,680 | B1 | 6/2001 | Miwa | 6,584,336 B1 | 6/2003 | Wassmund et al. |
| 6,248,083 | B1 | 6/2001 | Smith et al. | 6,589,171 B2 | 7/2003 | Keirsbilck |
| 6,251,076 | B1 | 6/2001 | Hovland et al. | 6,589,183 B2 | 7/2003 | Yokozeki |
| 6,251,080 | B1 | 6/2001 | Henkin et al. | 6,589,189 B2 | 7/2003 | Meyerson et al. |
| 6,251,081 | B1 | 6/2001 | Narimatsu | 6,594,513 B1 | 7/2003 | Jobsis et al. |
| 6,251,113 | B1 | 6/2001 | Appelbaum et al. | 6,597,933 B2 | 7/2003 | Kiani et al. |
| 6,256,523 | B1 | 7/2001 | Diab et al. | 6,605,038 B1 | 8/2003 | Teller et al. |
| 6,256,524 | B1 | 7/2001 | Walker et al. | 6,606,993 B1 | 8/2003 | Wiesmann et al. |
| 6,263,221 | B1 | 7/2001 | Chance et al. | 6,611,793 B1 | 8/2003 | Burnside et al. |
| 6,263,223 | B1 | 7/2001 | Shepherd et al. | 6,615,065 B1 * | 9/2003 | Barrett et al. .................. 600/340 |
| 6,280,213 | B1 | 8/2001 | Tobler et al. | 6,622,034 B1 | 9/2003 | Gorski et al. |
| 6,282,450 | B1 | 8/2001 | Hartlaub et al. | 6,626,537 B1 | 9/2003 | Odom et al. |
| 6,283,922 | B1 | 9/2001 | Goto et al. | 6,635,048 B1 | 10/2003 | Ullestad et al. |
| 6,285,895 | B1 | 9/2001 | Ristolainen et al. | 6,645,154 B2 | 11/2003 | Oka |
| 6,306,076 | B1 | 10/2001 | Gill | 6,645,155 B2 | 11/2003 | Inukai et al. |
| 6,308,089 | B1 | 10/2001 | von der Ruhr et al. | 6,654,622 B1 | 11/2003 | Eberhard et al. |
| 6,321,100 | B1 | 11/2001 | Parker | 6,666,860 B1 | 12/2003 | Takahashi |
| 6,322,516 | B1 | 11/2001 | Masuda et al. | 6,671,531 B2 | 12/2003 | Al-Ali et al. |
| 6,343,223 | B1 | 1/2002 | Chin | 6,678,543 B2 | 1/2004 | Diab et al. |
| 6,343,224 | B1 | 1/2002 | Parker | 6,681,454 B2 | 1/2004 | Modgil et al. |
| 6,346,886 | B1 | 2/2002 | DeLa Huerga | 6,684,091 B2 | 1/2004 | Parker |
| 6,349,228 | B1 | 2/2002 | Kiani et al. | 6,694,160 B2 | 2/2004 | Chin |
| 6,356,774 | B1 | 3/2002 | Bernstein et al. | 6,700,497 B2 | 3/2004 | Hibbs et al. |
| 6,362,622 | B1 | 3/2002 | Stauber et al. | 6,704,601 B1 | 3/2004 | Amely-Velez et al. |
| 6,368,282 | B1 | 4/2002 | Oka et al. | 6,708,048 B1 | 3/2004 | Chance |
| 6,370,411 | B1 | 4/2002 | Osadchy et al. | 6,711,425 B1 | 3/2004 | Reuss |
| 6,377,829 | B1 | 4/2002 | Al-Ali | 6,712,767 B2 | 3/2004 | Hossack et al. |
| 6,381,480 | B1 | 4/2002 | Stoddart et al. | 6,721,585 B1 | 4/2004 | Parker |
| 6,381,481 | B1 | 4/2002 | Levendowski et al. | 6,721,602 B2 | 4/2004 | Engmark et al. |
| 6,385,486 | B1 | 5/2002 | John et al. | 6,725,075 B2 | 4/2004 | Al-Ali |
| 6,385,821 | B1 | 5/2002 | Medgil et al. | 6,726,327 B2 | 4/2004 | Torrey et al. |
| 6,387,092 | B1 | 5/2002 | Burnside et al. | 6,731,963 B2 | 5/2004 | Finarov et al. |
| 6,388,240 | B2 | 5/2002 | Schulz et al. | 6,735,459 B2 | 5/2004 | Parker |
| 6,397,091 | B2 | 5/2002 | Diab et al. | 6,736,759 B1 | 5/2004 | Stubbs et al. |
| 6,405,075 | B1 | 6/2002 | Levin | 6,736,786 B1 | 5/2004 | Shabty et al. |
| 6,416,471 | B1 | 7/2002 | Kumar et al. | 6,743,173 B2 | 6/2004 | Penner et al. |
| 6,416,474 | B1 | 7/2002 | Penner et al. | 6,743,202 B2 | 6/2004 | Hirschman et al. |

| | | | | | |
|---|---|---|---|---|---|
| 6,745,061 B1 | 6/2004 | Hicks et al. | 7,248,910 B2 | 7/2007 | Li |
| 6,748,254 B2 | 6/2004 | O'Neil et al. | 7,289,837 B2 | 10/2007 | Mannheimer et al. |
| 6,763,255 B2 | 7/2004 | DeLonzer et al. | 7,297,119 B2 | 11/2007 | Westbrook et al. |
| 6,771,994 B2 | 8/2004 | Kiani et al. | 7,313,427 B2 | 12/2007 | Benni |
| 6,776,758 B2 | 8/2004 | Peszynski et al. | 7,349,726 B2 | 3/2008 | Casciani et al. |
| 6,779,257 B2 | 8/2004 | Kiepen et al. | 7,376,454 B2 | 5/2008 | Casciani et al. |
| 6,792,300 B1 | 9/2004 | Diab et al. | 7,415,298 B2 | 8/2008 | Casciani et al. |
| 6,796,946 B2 | 9/2004 | Ogura et al. | 2001/0000790 A1 | 5/2001 | Delonzer et al. |
| 6,804,543 B2 | 10/2004 | Miller et al. | 2001/0009265 A1 | 7/2001 | Schulz et al. |
| 6,808,496 B2 | 10/2004 | Oka et al. | 2001/0009398 A1 | 7/2001 | Sekura et al. |
| 6,811,538 B2 | 11/2004 | Westbrook et al. | 2001/0028309 A1 | 10/2001 | Torch |
| 6,813,511 B2 | 11/2004 | Diab et al. | 2001/0029325 A1 | 10/2001 | Parker |
| 6,824,520 B2 | 11/2004 | Orr et al. | 2001/0034506 A1 | 10/2001 | Hirschman et al. |
| 6,827,688 B2 | 12/2004 | Goto et al. | 2001/0037068 A1 | 11/2001 | Goto et al. |
| 6,830,711 B2 | 12/2004 | Mills et al. | 2001/0045532 A1 | 11/2001 | Schulz et al. |
| 6,832,987 B2 | 12/2004 | David et al. | 2001/0047126 A1 | 11/2001 | Nagai et al. |
| 6,842,722 B2 | 1/2005 | David | 2001/0048466 A1 | 12/2001 | Takami |
| 6,847,294 B1 | 1/2005 | Lin et al. | 2001/0051773 A1 | 12/2001 | Oka |
| 6,849,074 B2 | 2/2005 | Chen et al. | 2002/0005197 A1 | 1/2002 | DeVries et al. |
| 6,853,304 B2 | 2/2005 | Reisman et al. | 2002/0013538 A1 | 1/2002 | Teller |
| 6,870,479 B2 | 3/2005 | Gabriel | 2002/0013613 A1 | 1/2002 | Haller et al. |
| 6,893,400 B2 | 5/2005 | Kawaguchi et al. | 2002/0026107 A1 | 2/2002 | Kiani et al. |
| 6,898,299 B1 | 5/2005 | Brooks | 2002/0026109 A1 | 2/2002 | Diab et al. |
| 6,904,124 B2 | 6/2005 | Staver et al. | 2002/0032386 A1 | 3/2002 | Sackner et al. |
| 6,909,912 B2 | 6/2005 | Melker | 2002/0038082 A1 | 3/2002 | Chin |
| 6,911,027 B1 | 6/2005 | Edwards et al. | 2002/0042558 A1 | 4/2002 | Mendelson |
| 6,920,345 B2 | 7/2005 | Al-Ali et al. | 2002/0045807 A1 | 4/2002 | Al-Ali et al. |
| 6,921,198 B2 | 7/2005 | Gruszecki et al. | 2002/0049372 A1 | 4/2002 | Diab |
| 6,923,771 B2 | 8/2005 | Ogura et al. | 2002/0052539 A1 | 5/2002 | Haller et al. |
| 6,923,776 B2 | 8/2005 | Shabty et al. | 2002/0052552 A1 | 5/2002 | Jokozeki |
| 6,930,608 B2 | 8/2005 | Grajales et al. | 2002/0077535 A1 | 6/2002 | Finarov et al. |
| 6,934,570 B2 | 8/2005 | Kiani et al. | 2002/0082486 A1 | 6/2002 | Lavery et al. |
| 6,934,571 B2 | 8/2005 | Wiesmann et al. | 2002/0082489 A1 | 6/2002 | Casciani et al. |
| 6,936,011 B2 | 8/2005 | Sheldon | 2002/0082665 A1 | 6/2002 | Haller et al. |
| 6,939,314 B2 | 9/2005 | Hall et al. | 2002/0084904 A1 | 7/2002 | De La Huerga |
| 6,943,881 B2 | 9/2005 | Wang | 2002/0087087 A1 | 7/2002 | Oka et al. |
| 6,955,650 B2 | 10/2005 | Mault et al. | 2002/0091335 A1 | 7/2002 | John et al. |
| 6,965,071 B2 | 11/2005 | Watchko et al. | 2002/0091416 A1 | 7/2002 | Wassmund et al. |
| 6,971,790 B2 | 12/2005 | Quinn et al. | 2002/0091417 A1 | 7/2002 | Splett et al. |
| 6,985,763 B2 | 1/2006 | Boas et al. | 2002/0095087 A1 | 7/2002 | Mourad et al. |
| 6,985,764 B2 | 1/2006 | Mason et al. | 2002/0095092 A1 | 7/2002 | Kondo et al. |
| 6,990,371 B2 | 1/2006 | Powers et al. | 2002/0099268 A1 | 7/2002 | Paul et al. |
| 6,993,371 B2 | 1/2006 | Kiani et al. | 2002/0099298 A1 | 7/2002 | Yokozeki |
| 6,995,665 B2 | 2/2006 | Appelt et al. | 2002/0103445 A1 | 8/2002 | Rahdert et al. |
| 7,001,334 B2 | 2/2006 | Reed et al. | 2002/0109600 A1 | 8/2002 | Mault et al. |
| 7,018,338 B2 | 3/2006 | Vetter et al. | 2002/0111543 A1 | 8/2002 | Penner et al. |
| 7,020,508 B2 | 3/2006 | Stivoric et al. | 2002/0111777 A1 | 8/2002 | David |
| 7,024,235 B2 | 4/2006 | Melker et al. | 2002/0115919 A1 | 8/2002 | Al-Ali |
| 7,027,850 B2 | 4/2006 | Wasserman | 2002/0116797 A1 | 8/2002 | Modgil et al. |
| 7,027,871 B2 | 4/2006 | Burnes et al. | 2002/0124295 A1 | 9/2002 | Fenwick et al. |
| 7,039,449 B2 | 5/2006 | Al-Ali | 2002/0133066 A1 | 9/2002 | Miller et al. |
| 7,041,121 B1 | 5/2006 | Williams et al. | 2002/0133082 A1 | 9/2002 | Ogura |
| 7,047,054 B2 | 5/2006 | Benni | 2002/0135488 A1 | 9/2002 | Hibbs et al. |
| 7,047,055 B2 | 5/2006 | Boas et al. | 2002/0139368 A1 | 10/2002 | Bachinski |
| 7,047,056 B2 | 5/2006 | Hannula et al. | 2002/0148470 A1 | 10/2002 | Blue et al. |
| 7,048,687 B1 | 5/2006 | Reuss et al. | 2002/0151929 A1 | 10/2002 | Goto et al. |
| 7,054,453 B2 | 5/2006 | Causevic et al. | 2002/0156353 A1 | 10/2002 | Larson |
| 7,054,454 B2 | 5/2006 | Causevic et al. | 2002/0156354 A1 | 10/2002 | Larson |
| 7,063,669 B2 | 6/2006 | Brawner et al. | 2002/0156503 A1 | 10/2002 | Powers et al. |
| 7,067,893 B2 | 6/2006 | Mills et al. | 2002/0161290 A1 | 10/2002 | Chance |
| 7,072,704 B2 | 7/2006 | Bucholz et al. | 2002/0161305 A1 | 10/2002 | Oka |
| 7,079,036 B2 | 7/2006 | Cooper et al. | 2002/0161309 A1 | 10/2002 | Marro |
| 7,085,597 B2 | 8/2006 | Fein et al. | 2002/0165440 A1 | 11/2002 | Mason et al. |
| 7,087,023 B2 | 8/2006 | Daft et al. | 2002/0165462 A1 | 11/2002 | Westbrook et al. |
| 7,089,061 B2 | 8/2006 | Grey | 2002/0165590 A1 | 11/2002 | Crowe et al. |
| 7,096,052 B2 | 8/2006 | Mason et al. | 2002/0173706 A1 | 11/2002 | Takatani |
| 7,096,054 B2 | 8/2006 | Abdul-Hafiz et al. | 2002/0173708 A1 | 11/2002 | DeLonzer et al. |
| 7,097,621 B2 | 8/2006 | Narimatsu et al. | 2002/0188206 A1 | 12/2002 | Davis et al. |
| 7,107,706 B1 | 9/2006 | Bailey | 2002/0193692 A1 | 12/2002 | Inukai et al. |
| 7,113,815 B2 | 9/2006 | O'Neil et al. | 2003/0004445 A1 | 1/2003 | Hall et al. |
| RE39,359 E | 10/2006 | McGraw et al. | 2003/0004547 A1 | 1/2003 | Owen et al. |
| 7,127,278 B2 | 10/2006 | Melker et al. | 2003/0009083 A1 | 1/2003 | Takahashi |
| 7,132,641 B2 | 11/2006 | Schulz et al. | 2003/0009092 A1 | 1/2003 | Parker |
| 7,136,452 B2 | 11/2006 | Spartiotis et al. | 2003/0009119 A1 | 1/2003 | Kamm et al. |
| 7,171,251 B2 | 1/2007 | Sarussi et al. | 2003/0009308 A1 | 1/2003 | Kirtley |
| 7,181,264 B2 | 2/2007 | Wiesmann et al. | 2003/0018243 A1 | 1/2003 | Gerhardt et al. |
| 7,204,250 B1 | 4/2007 | Burton | 2003/0023140 A1 | 1/2003 | Chance |
| 7,220,220 B2 | 5/2007 | Stubbs et al. | 2003/0023146 A1 | 1/2003 | Shusterman |
| 7,245,953 B1 | 7/2007 | Parker | 2003/0023277 A1 | 1/2003 | Owen et al. |

| | | | | | | |
|---|---|---|---|---|---|---|
| 2003/0028105 A1 | 2/2003 | Miller | | 2004/0092919 A1 | 5/2004 | Ritchie et al. |
| 2003/0032887 A1 | 2/2003 | Harada et al. | | 2004/0100784 A1 | 5/2004 | Willers et al. |
| 2003/0032988 A1 | 2/2003 | Fincke | | 2004/0102931 A1 | 5/2004 | Ellis et al. |
| 2003/0040779 A1 | 2/2003 | Engmark et al. | | 2004/0114659 A1 | 6/2004 | Quinn et al. |
| 2003/0040820 A1 | 2/2003 | Stover et al. | | 2004/0117891 A1 | 6/2004 | Hannula et al. |
| 2003/0045785 A1 | 3/2003 | Diab et al. | | 2004/0122302 A1 | 6/2004 | Mason et al. |
| 2003/0045806 A1 | 3/2003 | Brydon | | 2004/0133088 A1 | 7/2004 | Al-Ali |
| 2003/0050551 A1 | 3/2003 | Shabty et al. | | 2004/0144391 A1 | 7/2004 | Brady et al. |
| 2003/0055308 A1 | 3/2003 | Friemel et al. | | 2004/0147822 A1 | 7/2004 | Al-Ali et al. |
| 2003/0062046 A1 | 4/2003 | Wiesmann et al. | | 2004/0147823 A1 | 7/2004 | Kiani et al. |
| 2003/0065269 A1 | 4/2003 | Vetter et al. | | 2004/0147974 A1 | 7/2004 | Engmark et al. |
| 2003/0065273 A1 | 4/2003 | Mault et al. | | 2004/0149282 A1 | 8/2004 | Hickle |
| 2003/0065274 A1 | 4/2003 | Mault et al. | | 2004/0158303 A1 | 8/2004 | Lennox et al. |
| 2003/0065275 A1 | 4/2003 | Mault et al. | | 2004/0160144 A1 | 8/2004 | Daft et al. |
| 2003/0066672 A1 | 4/2003 | Watchko et al. | | 2004/0162494 A1 | 8/2004 | Ogura et al. |
| 2003/0069508 A1 | 4/2003 | Kawaguchi et al. | | 2004/0163648 A1 | 8/2004 | Burton |
| 2003/0074037 A1 | 4/2003 | Moore et al. | | 2004/0168519 A1 | 9/2004 | Kalvensten et al. |
| 2003/0086156 A1 | 5/2003 | McGuire, Jr. | | 2004/0173456 A1 | 9/2004 | Boos et al. |
| 2003/0088203 A1 | 5/2003 | Gelfand et al. | | 2004/0186390 A1 | 9/2004 | Ross et al. |
| 2003/0088385 A1 | 5/2003 | David | | 2004/0221370 A1 | 11/2004 | Hannula et al. |
| 2003/0092999 A1 | 5/2003 | Goto et al. | | 2004/0230108 A1 | 11/2004 | Melker et al. |
| 2003/0097074 A1 | 5/2003 | Oka et al. | | 2004/0230116 A1 | 11/2004 | Cowan et al. |
| 2003/0105403 A1 | 6/2003 | Istvan et al. | | 2004/0231772 A1 | 11/2004 | Leonard et al. |
| 2003/0109775 A1* | 6/2003 | O'Neil et al. ............... 600/323 | | 2004/0236207 A1 | 11/2004 | Widener et al. |
| 2003/0116159 A1 | 6/2003 | Orr et al. | | 2004/0236224 A1 | 11/2004 | Stringer et al. |
| 2003/0120183 A1 | 6/2003 | Simmons | | 2004/0236242 A1 | 11/2004 | Graham et al. |
| 2003/0120271 A1 | 6/2003 | Burnside et al. | | 2004/0242981 A1 | 12/2004 | Pattisapu |
| 2003/0122706 A1 | 7/2003 | Choi et al. | | 2004/0252750 A1 | 12/2004 | Gruszecki et al. |
| 2003/0125616 A1 | 7/2003 | Black et al. | | 2004/0254490 A1 | 12/2004 | Egli |
| 2003/0132495 A1 | 7/2003 | Mills et al. | | 2004/0254501 A1 | 12/2004 | Mault |
| 2003/0135124 A1 | 7/2003 | Russell | | 2004/0254569 A1 | 12/2004 | Brosch et al. |
| 2003/0135127 A1 | 7/2003 | Sackner et al. | | 2004/0260161 A1 | 12/2004 | Melker et al. |
| 2003/0137425 A1 | 7/2003 | Gabriel | | 2004/0260191 A1 | 12/2004 | Stubbs et al. |
| 2003/0139641 A1 | 7/2003 | Hoedeman et al. | | 2004/0263337 A1 | 12/2004 | Terauchi et al. |
| 2003/0139656 A1 | 7/2003 | Kiani et al. | | 2004/0267104 A1 | 12/2004 | Hannula et al. |
| 2003/0139680 A1 | 7/2003 | Sheldon | | 2004/0267145 A1 | 12/2004 | David et al. |
| 2003/0143297 A1 | 7/2003 | Mills et al. | | 2005/0001728 A1 | 1/2005 | Appelt et al. |
| 2003/0144579 A1 | 7/2003 | Buss | | 2005/0012617 A1 | 1/2005 | DiSilvestro et al. |
| 2003/0144584 A1 | 7/2003 | Mendelson | | 2005/0015653 A1 | 1/2005 | Hajji et al. |
| 2003/0149366 A1 | 8/2003 | Stringer et al. | | 2005/0017864 A1 | 1/2005 | Tsoukalis |
| 2003/0153834 A1 | 8/2003 | Miller | | 2005/0020919 A1 | 1/2005 | Stringer et al. |
| 2003/0156288 A1 | 8/2003 | Barnum et al. | | 2005/0027207 A1 | 2/2005 | Westbrook et al. |
| 2003/0159844 A1 | 8/2003 | Wolf et al. | | 2005/0029432 A1 | 2/2005 | Bacarella et al. |
| 2003/0162414 A1 | 8/2003 | Schulz et al. | | 2005/0041531 A1 | 2/2005 | Sekura |
| 2003/0167080 A1 | 9/2003 | Hart et al. | | 2005/0043599 A1 | 2/2005 | O'Mara |
| 2003/0176810 A1 | 9/2003 | Maahs et al. | | 2005/0043763 A1 | 2/2005 | Marcovecchio et al. |
| 2003/0181799 A1 | 9/2003 | Lindekugel et al. | | 2005/0046575 A1 | 3/2005 | Cooper et al. |
| 2003/0189492 A1 | 10/2003 | Harvie | | 2005/0049465 A1 | 3/2005 | Wang |
| 2003/0208109 A1 | 11/2003 | David et al. | | 2005/0049501 A1 | 3/2005 | Conero et al. |
| 2003/0208128 A1 | 11/2003 | Hamilton et al. | | 2005/0059869 A1 | 3/2005 | Scharf et al. |
| 2003/0210149 A1 | 11/2003 | Reisman et al. | | 2005/0070776 A1 | 3/2005 | Mannheimer et al. |
| 2003/0212334 A1 | 11/2003 | Ogura et al. | | 2005/0070778 A1 | 3/2005 | Lakcey et al. |
| 2003/0214408 A1 | 11/2003 | Grajales et al. | | 2005/0070813 A1 | 3/2005 | Donofrio et al. |
| 2003/0216659 A1 | 11/2003 | Brawner et al. | | 2005/0075550 A1 | 4/2005 | Lindekugel |
| 2003/0216728 A1 | 11/2003 | Stern et al. | | 2005/0080345 A1 | 4/2005 | Finburgh et al. |
| 2003/0217972 A1 | 11/2003 | Connell et al. | | 2005/0085799 A1 | 4/2005 | Luria et al. |
| 2003/0225323 A1 | 12/2003 | Kiani et al. | | 2005/0090754 A1 | 4/2005 | Wolff et al. |
| 2003/0229276 A1 | 12/2003 | Sarussi et al. | | 2005/0096557 A1 | 5/2005 | Vosburgh et al. |
| 2003/0230307 A1 | 12/2003 | DeVries et al. | | 2005/0102167 A1 | 5/2005 | Kapoor |
| 2003/0233087 A1 | 12/2003 | Chen et al. | | 2005/0113650 A1 | 5/2005 | Pacione et al. |
| 2004/0002655 A1 | 1/2004 | Bolorforosh et al. | | 2005/0113656 A1 | 5/2005 | Chance |
| 2004/0004547 A1 | 1/2004 | Appelt et al. | | 2005/0113703 A1 | 5/2005 | Farringdon et al. |
| 2004/0007585 A1 | 1/2004 | Griffith et al. | | 2005/0114154 A1 | 5/2005 | Wolkowiez et al. |
| 2004/0030258 A1 | 2/2004 | Williams et al. | | 2005/0154299 A1 | 7/2005 | Hoctor et al. |
| 2004/0030323 A1 | 2/2004 | Ullestad et al. | | 2005/0171576 A1 | 8/2005 | Williams et al. |
| 2004/0035208 A1 | 2/2004 | Diaz et al. | | 2005/0182458 A1 | 8/2005 | Goedeke |
| 2004/0036854 A1 | 2/2004 | Fukuda et al. | | 2005/0188991 A1 | 9/2005 | Sun et al. |
| 2004/0039254 A1 | 2/2004 | Stivoric et al. | | 2005/0190068 A1 | 9/2005 | Gentry et al. |
| 2004/0039272 A1 | 2/2004 | Abdul-Hafiz et al. | | 2005/0197548 A1 | 9/2005 | Dietiker |
| 2004/0044286 A1 | 3/2004 | Hossack et al. | | 2005/0197550 A1 | 9/2005 | Al-Ali et al. |
| 2004/0044545 A1 | 3/2004 | Wiesmann et al. | | 2005/0206518 A1 | 9/2005 | Welch et al. |
| 2004/0047210 A1 | 3/2004 | Iwasaki | | 2005/0215847 A1 | 9/2005 | Heruth et al. |
| 2004/0054287 A1 | 3/2004 | Stephens | | 2005/0215880 A1 | 9/2005 | Harrison et al. |
| 2004/0054289 A1 | 3/2004 | Eberle et al. | | 2005/0215947 A1 | 9/2005 | Heruth et al. |
| 2004/0054291 A1 | 3/2004 | Schulz et al. | | 2005/0216064 A1 | 9/2005 | Heruth et al. |
| 2004/0064097 A1 | 4/2004 | Peterson | | 2005/0216199 A1 | 9/2005 | Banet |
| 2004/0064165 A1 | 4/2004 | Thompson | | 2005/0222522 A1 | 10/2005 | Heruth et al. |
| 2004/0082842 A1 | 4/2004 | Lumba et al. | | 2005/0222643 A1 | 10/2005 | Heruth et al. |
| 2004/0088027 A1 | 5/2004 | Burnes et al. | | 2005/0228234 A1 | 10/2005 | Yang |

| | | | | | | |
|---|---|---|---|---|---|---|
| 2005/0228296 A1 | 10/2005 | Banet | | 2006/0264725 A1 | 11/2006 | Hannula et al. |
| 2005/0228297 A1 | 10/2005 | Banet et al. | | 2006/0264726 A1 | 11/2006 | Mannheimer et al. |
| 2005/0231686 A1 | 10/2005 | Rathjen | | 2006/0264727 A1 | 11/2006 | Mannheimer et al. |
| 2005/0234312 A1 | 10/2005 | Suzuki et al. | | 2006/0264771 A1 | 11/2006 | Lin et al. |
| 2005/0234317 A1 | 10/2005 | Kiani | | 2006/0276700 A1 | 12/2006 | O'Neil et al. |
| 2005/0234518 A1 | 10/2005 | Heruth et al. | | 2006/0276701 A1 | 12/2006 | Ray |
| 2005/0240087 A1 | 10/2005 | Keenan et al. | | 2006/0281984 A1 | 12/2006 | Mannheimer et al. |
| 2005/0245797 A1 | 11/2005 | Al-Ali et al. | | 2007/0032732 A1 | 2/2007 | Shelley et al. |
| 2005/0256523 A1 | 11/2005 | Chen et al. | | 2007/0149871 A1 | 6/2007 | Sarussi et al. |
| 2005/0261594 A1 | 11/2005 | Banet | | 2007/0293746 A1 | 12/2007 | Sarussi et al. |
| 2005/0268916 A1 | 12/2005 | Mumford et al. | | 2008/0009691 A1 | 1/2008 | Parker |
| 2005/0272986 A1 | 12/2005 | Smith et al. | | 2008/0076988 A1 | 3/2008 | Sarussi et al. |
| 2005/0277819 A1 | 12/2005 | Kiani et al. | | 2008/0076990 A1 | 3/2008 | Sarussi et al. |
| 2005/0277821 A1 | 12/2005 | Payne et al. | | | | |
| 2005/0283082 A1 | 12/2005 | Geddes et al. | | FOREIGN PATENT DOCUMENTS | | |
| 2006/0009685 A1 | 1/2006 | Finarov et al. | | CN | 1657007 | 8/2005 |
| 2006/0009698 A1 | 1/2006 | Banet et al. | | DE | 3705493 | 8/1988 |
| 2006/0011199 A1 | 1/2006 | Rashad et al. | | DE | 3744781 A1 | 1/1989 |
| 2006/0020181 A1 | 1/2006 | Schmitt | | DE | 3810411 A1 | 10/1989 |
| 2006/0030049 A1 | 2/2006 | Bhimani et al. | | DE | 3927038 | 2/1991 |
| 2006/0030767 A1 | 2/2006 | Lang et al. | | DE | 4429845 C1 | 10/1995 |
| 2006/0036179 A1 | 2/2006 | Miller | | DE | 19541605 A1 | 5/1997 |
| 2006/0047447 A1 | 3/2006 | Brady et al. | | DE | 19939302 | 5/2001 |
| 2006/0058593 A1 | 3/2006 | Drinan et al. | | DE | 10029205 | 1/2002 |
| 2006/0058690 A1 | 3/2006 | Bartnik et al. | | EP | 0268850 | 6/1988 |
| 2006/0064133 A1 | 3/2006 | Von Arx et al. | | EP | 0 313 238 A1 | 10/1988 |
| 2006/0064134 A1 | 3/2006 | Mazar et al. | | EP | 0338518 | 10/1989 |
| 2006/0064142 A1 | 3/2006 | Chavan et al. | | EP | 0463620 | 1/1992 |
| 2006/0064143 A1 | 3/2006 | Von Arx et al. | | EP | 0 573 137 A1 | 2/1993 |
| 2006/0072645 A1 | 4/2006 | Quinn et al. | | EP | 0543172 A2 | 5/1993 |
| 2006/0074283 A1 | 4/2006 | Henderson et al. | | EP | 0 572 684 A1 | 8/1993 |
| 2006/0074324 A1 | 4/2006 | Wu et al. | | EP | 0578530 | 1/1994 |
| 2006/0084848 A1 | 4/2006 | Mitchnick | | EP | 0580385 A1 | 1/1994 |
| 2006/0084852 A1 | 4/2006 | Mason et al. | | EP | 0621026 A2 | 10/1994 |
| 2006/0085227 A1 | 4/2006 | Rosenfeld et al. | | EP | 0631756 | 1/1995 |
| 2006/0095032 A1 | 5/2006 | Jackson et al. | | EP | 0665025 A2 | 8/1995 |
| 2006/0100496 A1 | 5/2006 | Avron | | EP | 0 721 110 A1 | 7/1996 |
| 2006/0100530 A1 | 5/2006 | Kliot et al. | | EP | 1 683 478 A1 | 10/1999 |
| 2006/0100618 A1 | 5/2006 | Chan et al. | | EP | 0 695 139 A1 | 12/1999 |
| 2006/0122517 A1 | 6/2006 | Banet et al. | | EP | 0996063 | 4/2000 |
| 2006/0122520 A1 | 6/2006 | Banet et al. | | EP | 1048323 A2 | 11/2000 |
| 2006/0124128 A1 | 6/2006 | Deane et al. | | EP | 1 169 965 A1 | 6/2001 |
| 2006/0125623 A1 | 6/2006 | Appelt et al. | | EP | 1130412 A2 | 9/2001 |
| 2006/0132382 A1 | 6/2006 | Jannard | | EP | 0775311 B1 | 7/2002 |
| 2006/0133362 A1 | 6/2006 | Stein et al. | | FR | 2555744 | 5/1985 |
| 2006/0142640 A1 | 6/2006 | Takahashi | | FR | 002601137 A1 | 1/1988 |
| 2006/0149132 A1 | 7/2006 | Iddan | | GB | 834469 | 5/1960 |
| 2006/0149339 A1 | 7/2006 | Burnes et al. | | GB | 2135074 A | 8/1984 |
| 2006/0167351 A1 | 7/2006 | Isaacson et al. | | GB | 2390903 A | 1/2004 |
| 2006/0173247 A1 | 8/2006 | Medina | | JP | 55024614 A | 2/1980 |
| 2006/0183980 A1 | 8/2006 | Yang | | JP | 07336597 A | 12/1985 |
| 2006/0184051 A1 | 8/2006 | Hempstead et al. | | JP | 04057161 A | 2/1992 |
| 2006/0189859 A1 | 8/2006 | Kiani et al. | | JP | 08111295 A | 4/1996 |
| 2006/0195026 A1 | 8/2006 | Casciani et al. | | JP | 08112257 A | 5/1996 |
| 2006/0195027 A1 | 8/2006 | Casciani et al. | | JP | 08336546 A | 12/1996 |
| 2006/0195028 A1 | 8/2006 | Hannula et al. | | JP | 09010319 A | 1/1997 |
| 2006/0211929 A1 | 9/2006 | Casciani et al. | | JP | 9154937 A | 6/1997 |
| 2006/0211942 A1 | 9/2006 | Hoctor et al. | | JP | 10314149 A | 12/1998 |
| 2006/0217604 A1 | 9/2006 | Fein et al. | | JP | 11259583 A | 9/1999 |
| 2006/0217605 A1 | 9/2006 | Fein et al. | | JP | 2000/189440 A | 7/2000 |
| 2006/0217606 A1 | 9/2006 | Fein et al. | | JP | 2001/161648 A | 6/2001 |
| 2006/0217607 A1 | 9/2006 | Fein et al. | | JP | 2001-190498 A | 7/2001 |
| 2006/0217608 A1 | 9/2006 | Fein et al. | | JP | 2001-308576 A | 11/2001 |
| 2006/0224040 A1 | 10/2006 | Khait et al. | | JP | 2001-332832 A | 11/2001 |
| 2006/0224326 A1 | 10/2006 | St. Ores et al. | | JP | 2001/346775 A | 12/2001 |
| 2006/0224421 A1 | 10/2006 | St. Ores et al. | | JP | 2002/065647 A | 3/2002 |
| 2006/0229510 A1 | 10/2006 | Fein et al. | | JP | 2003/210402 A | 7/2003 |
| 2006/0229511 A1 | 10/2006 | Fein et al. | | JP | 2003/235813 A | 8/2003 |
| 2006/0229517 A1 | 10/2006 | Lin et al. | | JP | 2003/265425 A | 9/2003 |
| 2006/0241358 A1 | 10/2006 | Al-Ali et al. | | JP | 2004-16659 A | 1/2004 |
| 2006/0241384 A1 | 10/2006 | Fisher et al. | | JP | 2004/065832 A | 3/2004 |
| 2006/0241510 A1 | 10/2006 | Halperin et al. | | JP | 2004/121549 A | 4/2004 |
| 2006/0247504 A1 | 11/2006 | Tice | | JP | 2004258761 A | 9/2004 |
| 2006/0253010 A1 | 11/2006 | Brady et al. | | JP | 2005/013612 A | 1/2005 |
| 2006/0253953 A1 | 11/2006 | Williams | | JP | 2005/110816 A | 4/2005 |
| 2006/0258922 A1 | 11/2006 | Mason et al. | | JP | 2005/111187 A | 4/2005 |
| 2006/0264722 A1 | 11/2006 | Hannula et al. | | JP | 2005/143782 A | 5/2005 |
| 2006/0264723 A1 | 11/2006 | Hannula et al. | | JP | 2005/168600 A | 6/2005 |
| 2006/0264724 A1 | 11/2006 | Hannula et al. | | JP | 2005/266860 A | 9/2005 |

| | | | |
|---|---|---|---|
| JP | 2006/061178 A | 3/2006 |
| JP | 2006/066512 A | 3/2006 |
| JP | 2006/122693 A | 5/2006 |
| KR | 2003-195176 | 8/2002 |
| KR | 2005-292552 | 12/2004 |
| RU | 2000-337592 C1 | 6/1999 |
| RU | 2132204 | 6/1999 |
| WO | WO9001293 | 2/1990 |
| WO | WO9111137 | 8/1991 |
| WO | WO 91/15151 A1 | 10/1991 |
| WO | WO 91/18550 | 12/1991 |
| WO | WO 92/20273 | 11/1992 |
| WO | WO 95/06430 | 3/1995 |
| WO | WO9512349 | 5/1995 |
| WO | WO 96/15714 | 5/1996 |
| WO | WO 96/16591 A1 | 6/1996 |
| WO | WO 96/41138 A1 | 12/1996 |
| WO | WO 97/20494 | 6/1997 |
| WO | WO 97/20497 A1 | 6/1997 |
| WO | WO9817174 | 4/1998 |
| WO | WO9947039 | 9/1999 |
| WO | WO 99/63883 | 12/1999 |
| WO | WO0059374 | 10/2000 |
| WO | WO 00/78209 A1 | 12/2000 |
| WO | WO 01/01855 A1 | 1/2001 |
| WO | WO 01/17425 A2 | 3/2001 |
| WO | WO0176471 | 10/2001 |
| WO | WO 01/87224 A1 | 11/2001 |
| WO | WO 02/15784 A1 | 2/2002 |
| WO | WO 02/065901 A2 | 8/2002 |
| WO | WO 02/066977 A1 | 8/2002 |
| WO | WO 02/089664 | 11/2002 |
| WO | WO 02/089664 A2 | 11/2002 |
| WO | WO 03/026558 A2 | 4/2003 |
| WO | WO 03/057030 A1 | 7/2003 |
| WO | WO03071928 | 9/2003 |
| WO | WO 03/080152 A1 | 10/2003 |
| WO | WO 2004/030480 A1 | 4/2004 |
| WO | WO 2004/046673 A1 | 6/2004 |
| WO | WO 2004/084720 A2 | 10/2004 |
| WO | WO 2005/046466 A1 | 5/2005 |
| WO | WO 2005/079663 A1 | 9/2005 |
| WO | WO 2006/007231 | 1/2006 |
| WO | WO 2006/017117 A1 | 2/2006 |
| WO | WO 2006/021956 A2 | 3/2006 |
| WO | WO 2006/094108 A1 | 8/2006 |

OTHER PUBLICATIONS

U.S. Appl. No. 10/779,331, filed Feb. 13, 2004, Hannula et al.

* cited by examiner

US 7,979,102 B2

HAT-BASED OXIMETER SENSOR

CROSS REFERENCE TO RELATED APPLICATIONS

This application is a divisional of prior U.S. application Ser. No. 10/606,668, filed Jun. 25, 2003, the specification of which is incorporated by reference in its entirety.

BACKGROUND OF THE INVENTION

Field of the Invention

The present invention relates to optical oximeter sensors, and in particular to hat-based pulse oximeter sensors.

Many types of optical sensors are used to measure physiological characteristics of a patient. Typically, an optical sensor provides emitted light which is then scattered through a portion of a patient's tissue and detected. Various characteristics of a patient can be determined from analyzing such light, such as oxygen saturation, pulse rate, tissue bilirubin, etc.

Pulse oximetry is typically used to measure various blood flow characteristics including, but not limited to, the blood-oxygen saturation of hemoglobin in arterial blood, the volume of individual blood pulsations supplying the tissue, and the rate of blood pulsations corresponding to each heartbeat of a patient. Measurement of these characteristics has been accomplished by use of a non-invasive sensor which scatters light through a portion of the patient's tissue where blood perfuses the tissue, and photoelectrically senses the absorption of light in such tissue. The amount of light absorbed is then used to calculate the amount of blood constituent being measured.

The light scattered through the tissue is selected to be of one or more wavelengths that are absorbed by the blood in an amount representative of the amount of the blood constituent present in the blood. The amount of transmitted light scattered through the tissue will vary in accordance with the changing amount of blood constituent in the tissue and the related light absorption. For measuring blood oxygen level, such sensors have typically been provided with a light source that is adapted to generate light of at least two different wavelengths, and with photodetectors sensitive to both of those wavelengths, in accordance with known techniques for measuring blood oxygen saturation.

Known non-invasive sensors include devices that are secured to a portion of the body, such as a finger, an ear or the scalp. In animals and humans, the tissue of these body portions is perfused with blood and the tissue surface is readily accessible to the sensor.

Certain types of oximeter sensors are applied to a patient's forehead. To aid in the sensor's proper placement and the proper application of pressure by the sensor to the forehead site, some forehead sensors are maintained at the forehead site by either the assistance of an adhesive layer and/or a headband. While these approaches are helpful, there is still a need for an improved and easy way of placing, retaining, and locating the sensor on the forehead of its user.

BRIEF SUMMARY OF THE INVENTION

The present invention provides an oximeter sensor which will attach to a patient's forehead in an improved manner. In certain embodiments, the securing of the sensor to the forehead of the patient is achieved by attaching the sensor to the inside of hat which is worn by the patient when the sensor is in use.

In one embodiment, the present invention is an oximeter sensor, having: a substrate having a shape similar to a shape of at least a portion of a patient's forehead and including a section adapted to substantially fit over a portion of a forehead of a patient; an emitter disposed on the substrate at a position located on the section; and a detector disposed on the substrate at a distance from the emitter.

In one embodiment, the substrate is resilient and has a shape conformable to the forehead of a patient.

In one embodiment, the substrate includes an adhesive layer for adhering to the forehead of a patient.

In one embodiment, a hat is used for holding the sensor against the patient's forehead.

In one embodiment, the substrate is adhered to the inside of said hat.

In one embodiment, the substrate is adhesively attached to the inside of the hat. Alternately, the substrate is sewn into the hat.

In another embodiment, the present invention provides a method for determination of a blood characteristic, including: applying an emitter and a detector to spaced-apart positions on a forehead of a patient in the lower forehead region, above the eyebrow, with both the detector and the emitter placed above and predominantly lateral of the iris; securing the emitter and detector to the patient; emitting electromagnetic radiation with the emitter; detecting electromagnetic radiation scattered by the tissues of the forehead by the detector and producing a detector signal; and determining a blood characteristic in the patient from the detector signal.

In one embodiment, the securing of the emitter and the detector to the patient's forehead is achieved by attaching the emitter and the detector to an inside of a hat, and placing the hat on the head of the patient.

For a further understanding of the nature and advantages of the present invention, reference should be made to the following description in conjunction with the accompanying drawings.

DETAILED DESCRIPTION OF THE INVENTION

The embodiments of the present invention are directed towards configuring a reflectance-type oximeter sensor for placement in a hat in order to provide a relatively easy means of placing, retaining, and locating the sensor on the forehead of the user. With regard to the location of the sensor on the patient's forehead, it is preferred to have the sensor be located on the lower forehead region, above the eyebrow, with the sensor optics (emitter and detector) located above and predominantly lateral to or centered over the iris. The oximeter sensor can be attached to the inside band of a hat. The precise location of the reflectance sensor in the hat allows appropriate placement of the sensor in the optimal forehead location by a user not skilled in sensor placement. It has been found that the placement of a reflectance forehead sensor is a factor in the accurate determination of a blood flow characteristic, due to the vasculature of the forehead. In addition, it has been shown that having a certain amount of pressure on the forehead sensor can reduce the incidence of venous pulsations effects on the oximeter reading. The placement of the sensor in the band of the hat would minimize these issues, as the placement of a hat is fairly repeatable and predictable. A hat-based oximeter sensor as embodied by the present invention can be used on patients in clinical settings, or by athletes, soldiers, firemen, or in any environment where information related to a physiological parameter, such as heart rate or oxygen saturation information is desired.

Figure 1A:
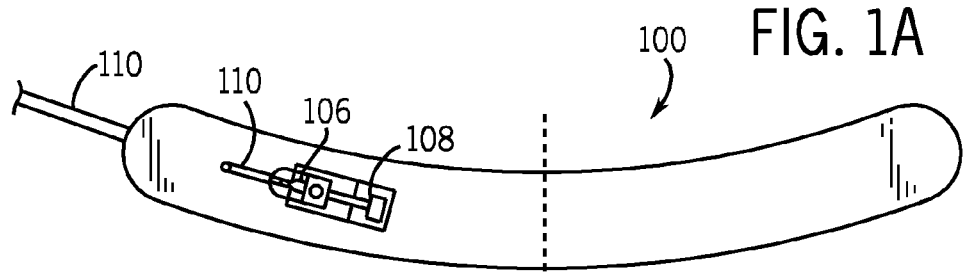
FIG. 1A is a top view of an embodiment of the sensor in accordance with the present disclosure with the face layer removed that can be placed within a hat or cap.
Figure 1B:
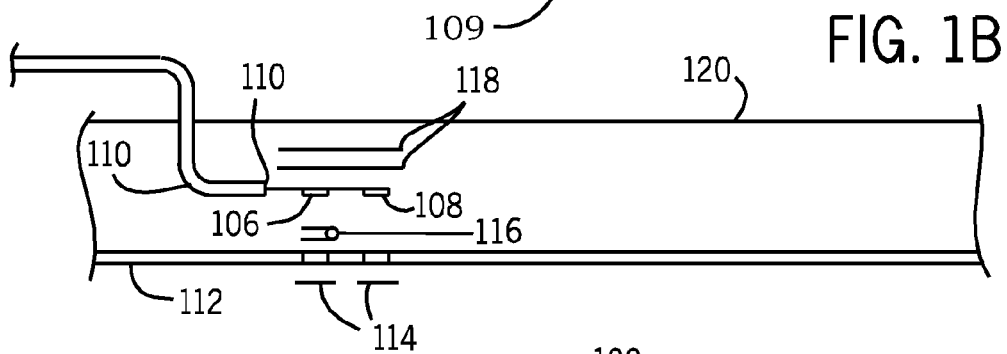
FIG. 1B is an internal cross-sectional view of an embodiment of the sensor in accordance with the present disclosure.
Figure 1C:
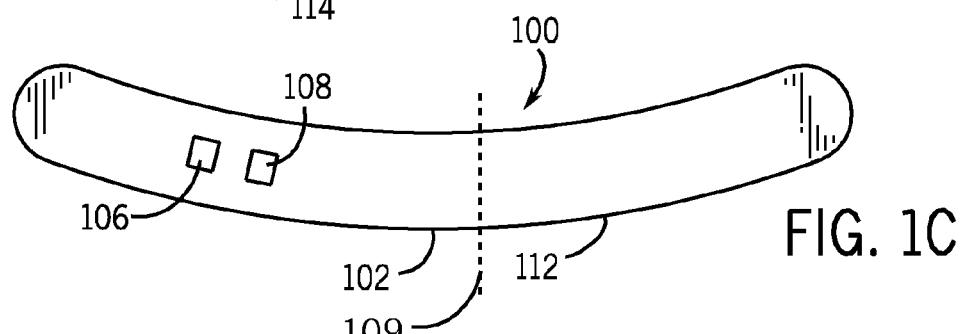
FIG. 1C is a top view of an embodiment of the face layer of the sensor in accordance with the present disclosure.
Figure 1D:
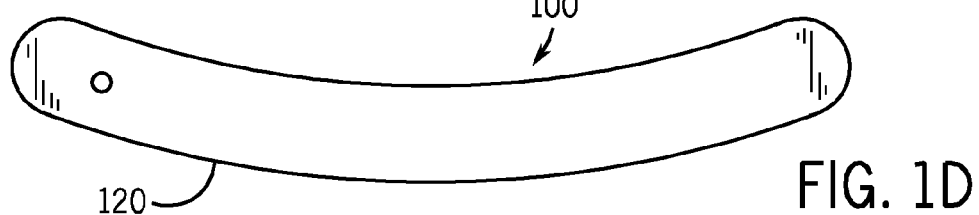
FIG. 1D is a top view of an embodiment of the back layer of the sensor in accordance with the present disclosure.
Figure 1E:
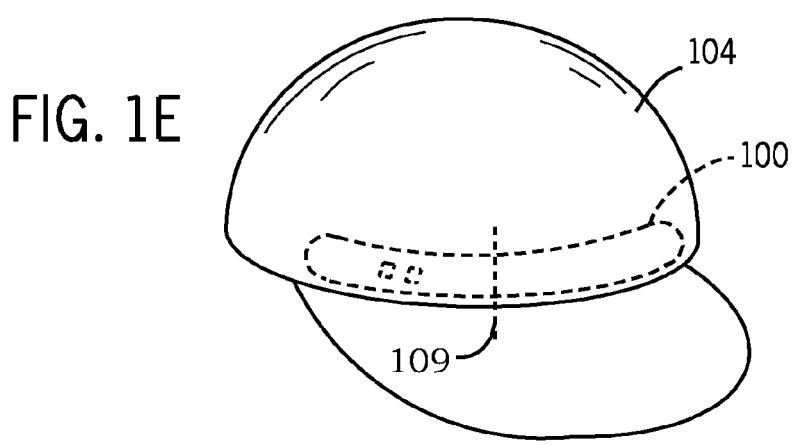
FIG. 1E is a perspective view of an embodiment of the sensor in accordance with the present disclosure placed within a hat.

FIG. 1A is a top view of an embodiment of a sensor 100 in accordance with the present disclosure with a face layer 112 removed that can be placed within a hat or cap. FIG. 1B shows the oximeter sensor 100 placed on a substrate 102, or face layer 112, that can be placed or adhered to the inside of a hat 104 as shown in FIG. 1E. As shown in FIG. 1E, the sensor 100, including the substrate 102, is arcuate both in three dimensions and in two dimensions. First, the substrate 102 may be conformable to a patient's forehead. In other words, the substrate 102 is arcuate in three dimensions to conform, for example, to the shape of the hat 104 placed on the patient's forehead. Second, as shown in the top views of FIGS. 1A and 1C, the substrate 102 is arcuate when flat against a planar surface in the absence of any restraining force. In other words, when the substrate 102 is flat in two dimensions, the substrate 102 has a curved shape. Moreover, the substrate 102 is not forced, held, conformed, or bent into an arcuate shape when flat, but is fabricated to remain arcuate without any external forces acting on the substrate 102. In the hat-based embodiment, the sensor uses an emitter 106, such as a light emitting diode (LED), containing two discrete wavelengths and a detector 108 placed more than 2 mm away, and ideally 10 mm-15 mm from the emitter. As shown in FIGS. 1A, 1C, and 1E, both the emitter 106 and the detector 108 are disposed to one side of an imaginary line 109 that bisects the substrate 102 through its arc. The substrate 102 can be black in order to minimize any shunting of light between sensor and patient skin. The sensor in a hat could be used in conjunction with a small, portable oximeter to allow mobility of the user during activities. Similarly, the sensor could be incorporated into a headband. Alternately, it may be desirable to provide a sensor with adhesive backing that would allow the user to place the sensor in a hat of their choice. Also shown in FIGS. 1A and 1B is a cable 110 for providing drive current to the LED and for providing the detector signal to the oximeter. The cable provides the electrical connection to the monitor; it also provides power for the emitter, signal carrying conductors from the detector, and shielding to protect the small signals from the detector against external electrical interference.

In FIG. 1B, the sensor is shown in a multi-layer structure having the face layer 112. The face layer 112 is the surface that is placed against the patient's skin. The face material may have an adhesive layer such as an acrylic or synthetic rubber adhesive, or it may be without adhesive, and typically made from a foam PVC or foam polyurethane material. The face layer 112 is preferably black so as to minimize the incidence of reflected light that does not go through the tissue. As shown in FIGS. 1B and 1C, the face layer 112 includes two windows 114. The windows 114 are generally a clear component, such as for example, a thin film or a clear molded plastic component that makes contact with the skin. The thin film window may be a polyurethane or an acrylic adhesive on a polyester film. The intent of the window 114 is to provide an efficient optical coupling mechanism between the optical components (emitter and detector) and the skin. As shown in FIG. 1B, located above the face 114, is a Faraday shield 116. The Faraday shield 116 is a conductive material, for example, a copper film or copper mesh, that is electrically connected to the monitor ground to help shield the detector from extraneous electrical interference while passing light to the detector. Next located are the LED 106 and the detector 108. Above the LED and the detector is a mask layer 118, which may include more than one mask layer. The mask layer 118 is generally a thin film that is intended to block light from entering the back side of the sensor, or from traveling directly from emitter to detector (shunt light). The purpose of the mask layer 118 is to ensure that all of the light reaching the detector is light from the emitter that has traveled through the capillary bed. Above the mask layer 118 is the back layer 120, shown separately in FIG. 1D. The back or the top layer is the non-tissue contacting surface of the sensor. This layer may include a cosmetic finish for the sensor, which can be white with some printed artwork identifying the sensor. Typical materials may be Velcro loop, or soft PVC foam. In a case where the sensor is mounted inside a hat or cap, as shown in FIG. 1E, the top layer is sometimes referred to as the back layer. In this case, the back layer may include a double stick adhesive so that it can be mounted inside the hat.

Figure 2A:
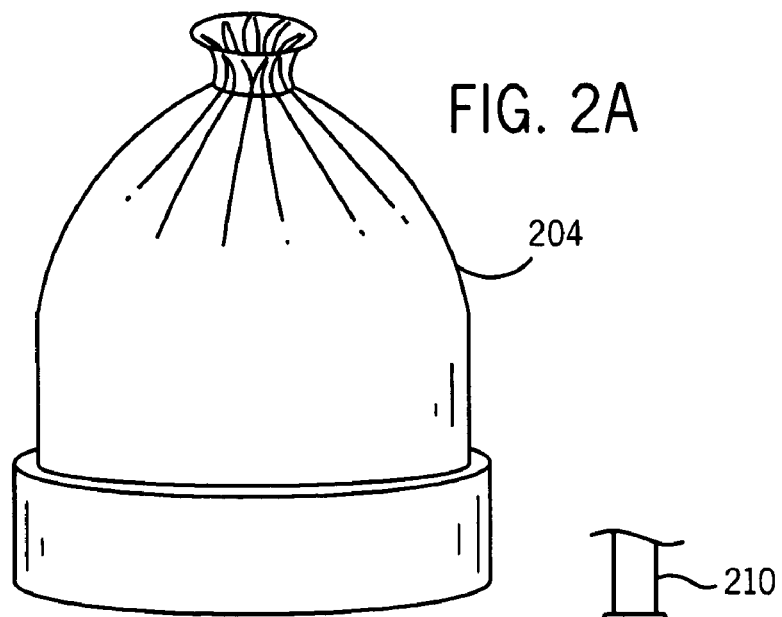
FIG. 2A is a perspective view of a stocking hat, with an embodiment of the sensor in accordance with the present disclosure shown mounted in the hat.
Figure 2B:
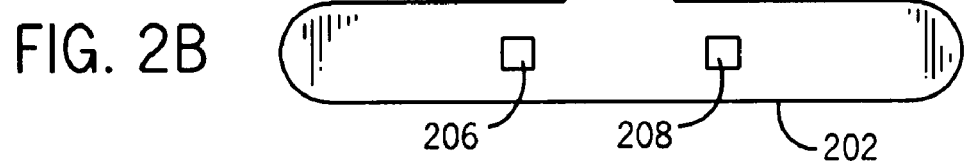
FIG. 2B is a top view of an embodiment of the sensor in accordance with the present disclosure.
Figure 2C:
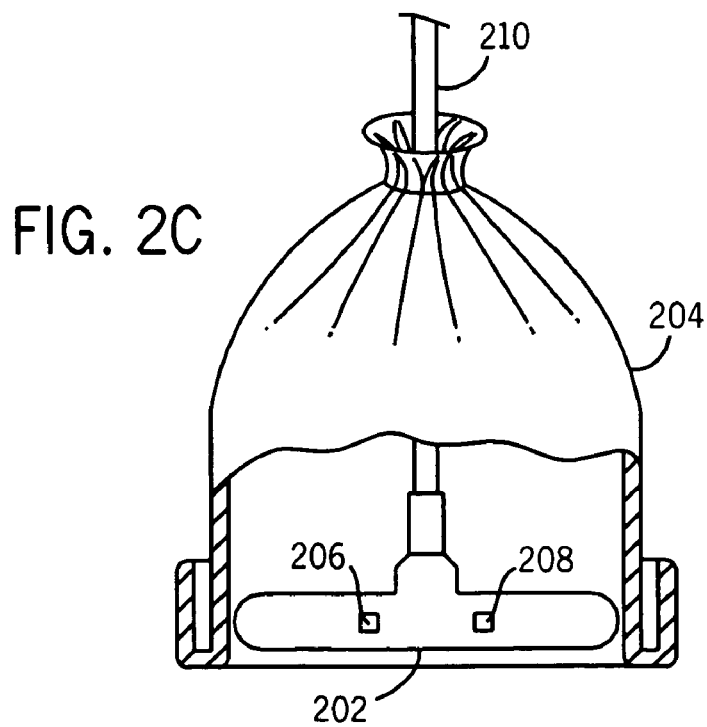
FIG. 2C is a partial cross-sectional view of an embodiment of the sensor in accordance with the present disclosure mounted in the hat.

FIG. 2A shows a top view of a stocking hat, with an embodiment of the sensor in accordance with the present disclosure shown mounted in the hat. This alternate embodiment of the present disclosure, is directed towards the placement of a small reflectance sensor 202 in a stocking cap or beanie 204 as shown in FIG. 2C. FIGS. 2B and 2C show the sensor carrier layer 202 holding an LED 206 and a detector 208 and a cable 210, similar to the ones described above in conjunction with FIGS. 1A-1E. This embodiment may be used for neonates. This embodiment would allow easy placement of a sensor on the forehead of a patient while applying a predictable pressure on the sensor. The sensor in a hat also resolves a concern about the cosmetic appearance of having a sensor on the forehead of the patient. A sensor in a stocking cap is much more acceptable to a parent than having a sensor located on the forehead. Depending on the tension of the stocking cap, provided by its own stretchiness or by an adjustable integral headband strap, the sensor may have a light tack adhesive, or no adhesive at all. The lack of an adhesive layer is a desirable feature, especially on neonates as adhesives may sometimes leave visible damage to the fragile skin of a neonate.

Figure 3A:
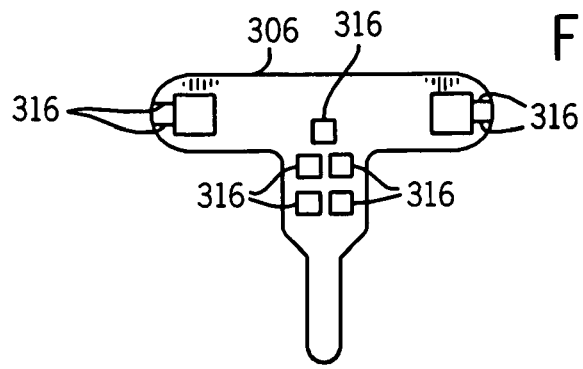
FIG. 3A is a top view of an embodiment of the flex circuit of the sensor in accordance with the present disclosure.
Figure 3B:
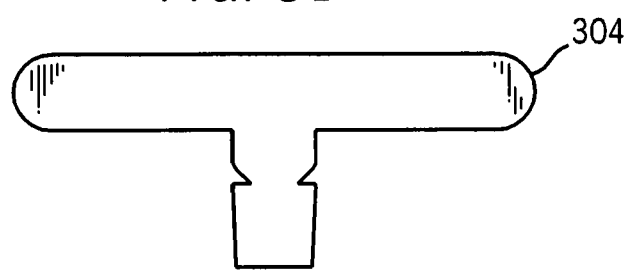
FIG. 3B is a top view of an embodiment of the top layer of the sensor in accordance with the present disclosure.
Figure 3C:
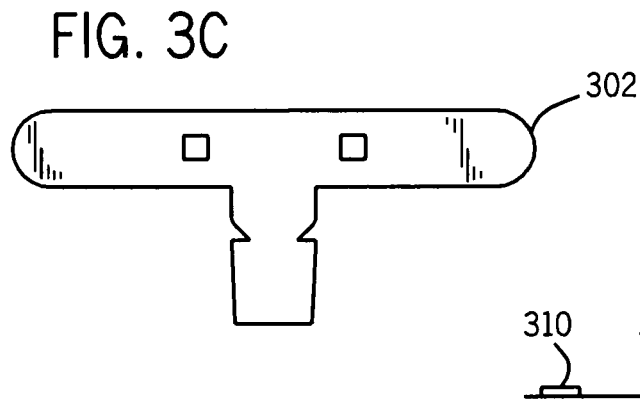
FIG. 3C is a top view of an embodiment of the face layer of the sensor in accordance with the present disclosure.
Figure 3D:
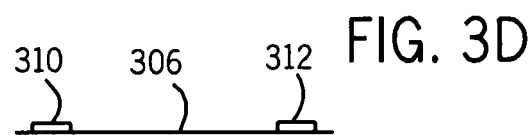
FIG. 3D is a side view of an embodiment of the flex circuit of the sensor in accordance with the present disclosure.
Figure 3F:
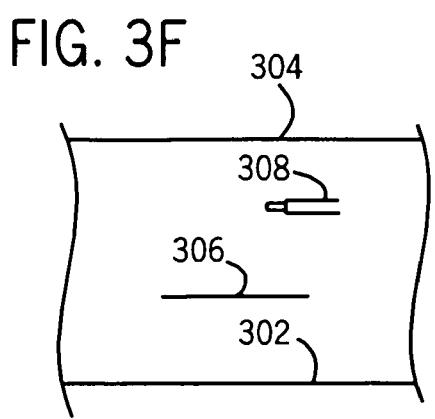
FIG. 3F is an internal view of an embodiment of the sensor in accordance with the present disclosure.
Figure 3E:
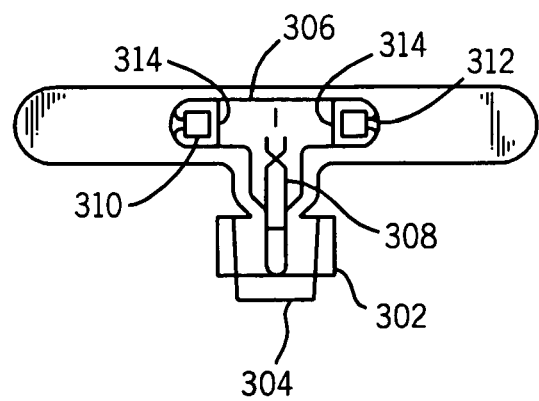
FIG. 3E is a top view of an embodiment of the sensor in accordance with the present disclosure with the top layer removed.

FIG. 3E is a top view of an embodiment of the sensor in accordance with the present disclosure with the top layer removed. FIG. 3F shows that the sensor portion generally includes a face layer 302, a top layer 304 and a flex circuit 306 that is placed between the face and top layers. The top layer 304 is shown separately in FIG. 3B and the face layer 302 is shown separately in FIG. 3C. Also shown in FIG. 3E is a multi-layer unassembled view showing the relative positions of the face 302, flex circuit 306, a cable 308 and the top layer 304. The flex circuit layer 306 holds the emitter (LED) 310 and the detector 312 as well as the mask layer 314 and Faraday shield as described above. FIG. 3D shows a side view of the flex circuit 306. As shown in FIG. 3A, the flex circuit 306 also has several holes 316 to allow for electrical connections between the leads in the cable and the LED and the detector.

As will be understood by those skilled in the art, the present invention may be embodied in other specific forms without departing from the essential characteristics thereof. For example, the sensor may include adhesive layers for adhering to the inside of a hat or the user's skin, or that that the sensor may be sewn into the hat. These other embodiments are intended to be included within the scope of the present invention, which is set forth in the following claims.

What is claimed is:

1. A pulse oximetry sensor adapted for use on a patient's forehead comprising:
   a substrate conformable to a patient's forehead, wherein the substrate is arcuate when placed flat upon a planar surface in the absence of any restraining force;
   an emitter disposed on the substrate; and
   a detector disposed on the substrate, wherein both the emitter and the detector are disposed to one side of an imaginary line that bisects the substrate through its arc.

2. The sensor of claim 1, comprising a hat or cap, wherein the substrate is associated with the hat or cap and configured to be positioned on the patient in a predetermined position.

3. The sensor of claim 2, wherein the predetermined position comprises a lower forehead region.

4. The sensor of claim 2, wherein the predetermined position comprises a position substantially centering the emitter and the detector above the patient's iris.

5. The sensor of claim 2, wherein the predetermined position comprises a position wherein the emitter and the detector are lateral to the patient's iris.

6. The sensor of claim 1, wherein the substrate comprises an adhesive layer adapted to contact the patient's forehead.

7. The sensor of claim 1, wherein the emitter comprises at least one light emitting diode.

8. The sensor of claim 1, wherein the detector comprises at least one photodetector.

9. The sensor of claim 1, wherein the emitter and detector are disposed asymmetrically on the substrate in relation to one another.

10. The sensor of claim 1, comprising a cable disposed on the substrate.

11. A method of manufacturing a pulse oximetry sensor comprising:
    providing a substrate conformable to a patient's forehead, wherein the substrate is arcuate when placed flat upon a planar surface in the absence of any restraining force;
    providing an emitter disposed on the substrate; and
    providing a detector disposed on the substrate, wherein both the emitter and the detector are disposed to one side of an imaginary line that bisects the substrate through its arc.

12. The method of claim 11, comprising configuring the substrate to be positioned on the patient in a predetermined position, wherein the substrate is associated with a hat or cap.

13. The method of claim 12, wherein the predetermined position comprises a lower forehead region.

14. The method of claim 12, wherein the predetermined position comprises a position substantially centering the emitter and the detector above the patient's iris.

15. The method of claim 12, wherein the predetermined position comprises a position wherein the emitter and the detector are lateral to the patient's iris.

16. The method of claim 11, comprising providing the substrate having an adhesive layer adapted to contact the patient's forehead.

17. The method of claim 11, wherein the emitter comprises at least one light emitting diode.

18. The method of claim 11, wherein the detector comprises at least one photodetector.

19. The method of claim 11, wherein the emitter and detector are disposed asymmetrically on the substrate in relation to one another.

20. The method of claim 11, comprising providing a cable disposed on the substrate.

* * * * *